(12) United States Patent
Singhal et al.

(10) Patent No.: US 8,280,478 B2
(45) Date of Patent: *Oct. 2, 2012

(54) EVALUATION OF IMPLANTATION SITE FOR IMPLANTATION OF IMPLANTABLE MEDICAL DEVICE

(75) Inventors: Ruchika Singhal, Minneapolis, MN (US); Carl D. Wahlstrand, Lino Lakes, MN (US); Robert M. Skime, Coon Rapids, MN (US); Steven J. Urquhart, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/538,605

(22) Filed: Aug. 10, 2009

(65) Prior Publication Data
US 2009/0299380 A1     Dec. 3, 2009

Related U.S. Application Data

(62) Division of application No. 10/835,527, filed on Apr. 29, 2004, now Pat. No. 7,596,399.

(51) Int. Cl.
*A61B 5/04* (2006.01)
*A61B 6/00* (2006.01)
(52) U.S. Cl. .................... 600/377; 600/378; 600/427
(58) Field of Classification Search .................. 600/407, 600/411, 416, 427, 311, 377–378, 383
See application file for complete search history.

(56) References Cited

U.S. PATENT DOCUMENTS

| | | |
|---|---|---|
| 3,310,051 A | 3/1967 | Schulte |
| 3,522,811 A | 8/1970 | Schwartz et al. |
| 3,690,325 A | 9/1972 | Kenny |
| 3,720,874 A | 3/1973 | Gorcik et al. |
| 3,724,467 A | 4/1973 | Avery et al. |
| 3,888,260 A | 6/1975 | Fischell |
| 3,913,587 A | 10/1975 | Newash |
| 3,941,135 A | 3/1976 | von Sturm et al. |

(Continued)

FOREIGN PATENT DOCUMENTS
DE    3940632    12/1990
(Continued)

OTHER PUBLICATIONS

U.S. Appl. No. 12/538,623, filed Aug. 10, 2009, entitled "Implantation of Implantable Medical Device," by Singhal et al.

(Continued)

*Primary Examiner* — Niketa Patel
*Assistant Examiner* — Catherine Voorhees
(74) *Attorney, Agent, or Firm* — Shumaker & Sieffert, P.A.

(57) ABSTRACT

In general, the invention is directed to strategies pertaining to implantation of an implantable medical device between a scalp and a skull of the patient. The invention pertains to collection of data such as data pertaining to the skull of the patient, the scalp of the patient, the vascular structure or neurological structures in the head of the patient, and the like. The data may be in the form of images, such as images generated by X-ray, magnetic resonance imaging, CT-scan and fluoroscopy. A surgeon can use the collected data to determine, for example, whether the patient is a candidate for a cranial implantation, whether the patient's skull and scalp can support the implantation, what configuration of device should be implanted, where the device should be implanted, and how the surgical incisions should be made.

45 Claims, 10 Drawing Sheets

U.S. PATENT DOCUMENTS

| | | | |
|---|---|---|---|
| 4,006,748 A | 2/1977 | Schulman | |
| 4,010,760 A | 3/1977 | Kraska et al. | |
| 4,013,081 A | 3/1977 | Kolenik | |
| 4,040,412 A | 8/1977 | Sato | |
| 4,094,321 A | 6/1978 | Muto | |
| 4,256,115 A | 3/1981 | Bilitch | |
| 4,266,552 A | 5/1981 | Dutcher et al. | |
| 4,328,813 A | 5/1982 | Ray | |
| 4,399,819 A | 8/1983 | Cowdery | |
| 4,399,820 A | 8/1983 | Wirtzfeld et al. | |
| 4,408,607 A | 10/1983 | Maurer | |
| 4,499,907 A | 2/1985 | Kallok et al. | |
| 4,503,860 A | 3/1985 | Sams et al. | |
| 4,574,780 A | 3/1986 | Manders | |
| 4,616,655 A | 10/1986 | Weinberg et al. | |
| 4,911,178 A | 3/1990 | Neal | |
| 4,928,696 A | 5/1990 | Henderson et al. | |
| 4,934,368 A | 6/1990 | Lynch | |
| 4,969,899 A | 11/1990 | Cox, Jr. | |
| 4,972,846 A | 11/1990 | Owens et al. | |
| 5,085,644 A | 2/1992 | Watson et al. | |
| 5,116,345 A | 5/1992 | Jewell et al. | |
| 5,144,946 A | 9/1992 | Weinberg et al. | |
| 5,197,332 A | 3/1993 | Shennib | |
| 5,220,929 A | 6/1993 | Marquit | |
| 5,252,090 A | 10/1993 | Giurtino et al. | |
| 5,271,397 A | 12/1993 | Seligman et al. | |
| 5,312,440 A | 5/1994 | Hirschberg et al. | |
| 5,314,451 A | 5/1994 | Mulier | |
| 5,314,453 A | 5/1994 | Jeutter | |
| 5,396,813 A | 3/1995 | Takeuchi et al. | |
| 5,411,538 A | 5/1995 | Lin | |
| H1465 H | 7/1995 | Stokes | |
| 5,431,695 A | 7/1995 | Wiklund et al. | |
| 5,433,734 A | 7/1995 | Stokes et al. | |
| 5,455,999 A | 10/1995 | Owens et al. | |
| 5,456,698 A | 10/1995 | Byland et al. | |
| 5,458,997 A | 10/1995 | Crespi et al. | |
| 5,477,855 A | 12/1995 | Schindler et al. | |
| 5,480,416 A | 1/1996 | Garcia et al. | |
| 5,489,225 A | 2/1996 | Julian | |
| 5,554,194 A | 9/1996 | Sanders | |
| 5,562,715 A | 10/1996 | Czura et al. | |
| 5,571,148 A | 11/1996 | Loeb et al. | |
| 5,573,551 A | 11/1996 | Lin et al. | |
| 5,613,935 A | 3/1997 | Jarvik | |
| 5,638,832 A | 6/1997 | Singer et al. | |
| 5,645,586 A | 7/1997 | Meltzer | |
| 5,674,260 A | 10/1997 | Weinberg | |
| 5,678,559 A | 10/1997 | Drakulic | |
| 5,702,430 A | 12/1997 | Slimon et al. | |
| 5,741,313 A | 4/1998 | Nason et al. | |
| 5,748,767 A * | 5/1998 | Raab | 382/128 |
| 5,755,743 A | 5/1998 | Volz et al. | |
| 5,769,874 A | 6/1998 | Dahlberg | |
| 5,776,169 A | 7/1998 | Schroeppel | |
| 5,792,067 A | 8/1998 | Karell | |
| 5,800,535 A | 9/1998 | Howard, III | |
| 5,814,095 A | 9/1998 | Leysieffer et al. | |
| 5,836,935 A | 11/1998 | Ashton et al. | |
| 5,843,150 A | 12/1998 | Adams et al. | |
| 5,873,899 A | 2/1999 | Stutz, Jr. et al. | |
| RE36,120 E | 3/1999 | Karell | |
| 5,876,424 A | 3/1999 | O'Phelan et al. | |
| 5,895,414 A | 4/1999 | Sanchez-Zambrano | |
| 5,896,647 A | 4/1999 | Shkuratoff | |
| 5,919,215 A | 7/1999 | Haeg et al. | |
| 5,935,154 A | 8/1999 | Westlund | |
| 5,941,905 A | 8/1999 | Single | |
| 5,941,906 A | 8/1999 | Barreras, Sr. et al. | |
| 5,954,751 A | 9/1999 | Chen et al. | |
| 5,954,757 A | 9/1999 | Gray | |
| 5,958,088 A | 9/1999 | Vu et al. | |
| 5,984,859 A | 11/1999 | Lesinski | |
| 5,991,664 A | 11/1999 | Seligman | |
| 6,006,124 A | 12/1999 | Fischell et al. | |
| 6,016,449 A | 1/2000 | Fischell et al. | |
| 6,016,593 A | 1/2000 | Kyrstein | |
| 6,044,304 A | 3/2000 | Baudino | |
| 6,061,593 A | 5/2000 | Fischell et al. | |
| 6,067,474 A | 5/2000 | Schulman et al. | |
| 6,091,979 A | 7/2000 | Madsen | |
| 6,106,464 A | 8/2000 | Bass et al. | |
| 6,128,538 A | 10/2000 | Fischell et al. | |
| 6,131,581 A | 10/2000 | Leysieffer et al. | |
| 6,134,474 A | 10/2000 | Fischell et al. | |
| 6,146,390 A * | 11/2000 | Heilbrun et al. | 606/130 |
| 6,154,677 A | 11/2000 | Leysieffer | |
| 6,162,487 A | 12/2000 | Darouiche | |
| 6,168,580 B1 | 1/2001 | Yardley | |
| 6,176,879 B1 | 1/2001 | Leysieffer et al. | |
| 6,205,358 B1 | 3/2001 | Haeg et al. | |
| 6,214,032 B1 | 4/2001 | Loeb et al. | |
| 6,218,016 B1 | 4/2001 | Tedeschi et al. | |
| 6,230,049 B1 | 5/2001 | Fischell et al. | |
| 6,233,488 B1 | 5/2001 | Hess | |
| 6,248,080 B1 | 6/2001 | Miesel et al. | |
| 6,248,126 B1 | 6/2001 | Lesser et al. | |
| 6,259,951 B1 | 7/2001 | Kuzma et al. | |
| 6,263,225 B1 | 7/2001 | Howard, III | |
| 6,266,556 B1 | 7/2001 | Ives et al. | |
| 6,269,266 B1 | 7/2001 | Leysieffer | |
| 6,272,382 B1 | 8/2001 | Lenarz et al. | |
| 6,283,997 B1 * | 9/2001 | Garg et al. | 623/16.11 |
| 6,308,101 B1 | 10/2001 | Gord et al. | |
| 6,324,428 B1 | 11/2001 | Weinberg et al. | |
| 6,324,433 B1 | 11/2001 | Errico | |
| 6,330,468 B1 | 12/2001 | Scharf | |
| 6,354,299 B1 | 3/2002 | Fischell et al. | |
| 6,356,792 B1 | 3/2002 | Zonenshayn et al. | |
| 6,358,281 B1 | 3/2002 | Berrang et al. | |
| 6,360,122 B1 | 3/2002 | Fischell et al. | |
| 6,366,813 B1 | 4/2002 | DiLorenzo | |
| 6,405,079 B1 | 6/2002 | Ansarinia | |
| 6,415,184 B1 | 7/2002 | Ishikawa et al. | |
| 6,427,086 B1 | 7/2002 | Upton et al. | |
| 6,436,422 B1 | 8/2002 | Trogolo et al. | |
| 6,445,956 B1 | 9/2002 | Laird et al. | |
| 6,456,256 B1 | 9/2002 | Amundson et al. | |
| 6,456,886 B1 | 9/2002 | Howard et al. | |
| 6,480,743 B1 | 11/2002 | Kirkpatrick et al. | |
| 6,490,486 B1 | 12/2002 | Bradley | |
| 6,498,951 B1 | 12/2002 | Larson et al. | |
| 6,505,077 B1 | 1/2003 | Kast et al. | |
| 6,516,227 B1 | 2/2003 | Meadows et al. | |
| 6,516,808 B2 | 2/2003 | Schulman | |
| 6,517,476 B1 | 2/2003 | Bedoya et al. | |
| 6,537,200 B2 | 3/2003 | Leysieffer et al. | |
| 6,554,762 B2 | 4/2003 | Leysieffer | |
| 6,560,486 B1 | 5/2003 | Frei et al. | |
| 6,565,503 B2 | 5/2003 | Leysieffer et al. | |
| 6,567,703 B1 | 5/2003 | Thompson et al. | |
| 6,575,894 B2 | 6/2003 | Leysieffer et al. | |
| 6,597,954 B1 | 7/2003 | Pless et al. | |
| 6,618,623 B1 | 9/2003 | Pless et al. | |
| 6,626,680 B2 | 9/2003 | Ciurzynski et al. | |
| 6,648,914 B2 | 11/2003 | Berrang et al. | |
| 6,671,544 B2 | 12/2003 | Baudino | |
| 6,726,678 B1 | 4/2004 | Nelson et al. | |
| 6,736,770 B2 | 5/2004 | Leysieffer et al. | |
| 6,782,292 B2 | 8/2004 | Whitehurst | |
| 6,788,974 B2 | 9/2004 | Bardy et al. | |
| 6,805,998 B2 | 10/2004 | Jenson et al. | |
| 6,850,802 B2 | 2/2005 | Holsheimer | |
| 6,882,881 B1 | 4/2005 | Lesser et al. | |
| 6,899,976 B2 | 5/2005 | Larson et al. | |
| 6,963,780 B2 | 11/2005 | Ruben et al. | |
| 6,994,933 B1 | 2/2006 | Bates | |
| 7,003,352 B1 | 2/2006 | Whitehurst | |
| 7,010,351 B2 | 3/2006 | Firlik et al. | |
| 7,033,326 B1 | 4/2006 | Pianca et al. | |
| 7,103,415 B2 | 9/2006 | Probst et al. | |
| 7,107,097 B2 | 9/2006 | Stern et al. | |
| 7,110,819 B1 | 9/2006 | O'Hara | |
| 7,167,760 B2 * | 1/2007 | Dawant et al. | 607/116 |
| 7,212,864 B2 | 5/2007 | Wahlstrand et al. | |
| 7,242,982 B2 | 7/2007 | Singhal et al. | |

| | | |
|---|---|---|
| 7,263,401 B2 | 8/2007 | Scott et al. |
| 7,596,399 B2 | 9/2009 | Singhal et al. |
| 7,702,380 B1 | 4/2010 | Dean |
| 8,095,200 B2 * | 1/2012 | Quaid, III ............... 600/407 |
| 2001/0033953 A1 | 10/2001 | Takeuchi et al. |
| 2001/0051819 A1 | 12/2001 | Fischell et al. |
| 2002/0002390 A1 | 1/2002 | Fischell et al. |
| 2002/0013612 A1 | 1/2002 | Whitehurst |
| 2002/0019669 A1 | 2/2002 | Berrang et al. |
| 2002/0042630 A1 | 4/2002 | Bardy et al. |
| 2002/0042634 A1 | 4/2002 | Bardy et al. |
| 2002/0051550 A1 | 5/2002 | Leysieffer |
| 2002/0059049 A1 * | 5/2002 | Bradbury et al. ............. 703/11 |
| 2002/0068958 A1 | 6/2002 | Bardy et al. |
| 2002/0072770 A1 | 6/2002 | Pless |
| 2002/0077670 A1 | 6/2002 | Archer et al. |
| 2002/0087201 A1 | 7/2002 | Firlik et al. |
| 2002/0099412 A1 | 7/2002 | Fischell et al. |
| 2002/0103510 A1 | 8/2002 | Bardy et al. |
| 2002/0107546 A1 | 8/2002 | Ostroff et al. |
| 2002/0147498 A1 * | 10/2002 | Tallarida et al. ........ 623/20.14 |
| 2002/0161403 A1 | 10/2002 | Meadows et al. |
| 2002/0165588 A1 | 11/2002 | Fraley et al. |
| 2002/0169485 A1 | 11/2002 | Pless et al. |
| 2002/0177882 A1 | 11/2002 | DiLorenzo |
| 2003/0004428 A1 * | 1/2003 | Pless et al. ................. 600/544 |
| 2003/0004546 A1 | 1/2003 | Casey |
| 2003/0040781 A1 | 2/2003 | Sunderland et al. |
| 2003/0073972 A1 | 4/2003 | Rosenman et al. |
| 2003/0085684 A1 | 5/2003 | Tsukamoto et al. |
| 2003/0088294 A1 | 5/2003 | Gesotti |
| 2003/0109903 A1 | 6/2003 | Berrang et al. |
| 2003/0120320 A1 | 6/2003 | Solom |
| 2003/0125786 A1 | 7/2003 | Gliner et al. |
| 2003/0130706 A1 | 7/2003 | Sheffield et al. |
| 2003/0171787 A1 | 9/2003 | Money et al. |
| 2003/0204229 A1 | 10/2003 | Stokes |
| 2003/0228042 A1 * | 12/2003 | Sinha ........................ 382/131 |
| 2004/0015070 A1 | 1/2004 | Liang et al. |
| 2004/0030245 A1 | 2/2004 | Noble et al. |
| 2004/0082977 A1 | 4/2004 | Engmark et al. |
| 2004/0102828 A1 | 5/2004 | Lowry et al. |
| 2004/0172090 A1 | 9/2004 | Janzig et al. |
| 2004/0173221 A1 | 9/2004 | Singhal et al. |
| 2004/0176673 A1 | 9/2004 | Wahlstrand et al. |
| 2004/0176750 A1 | 9/2004 | Nelson et al. |
| 2004/0176815 A1 | 9/2004 | Janzig et al. |
| 2004/0176816 A1 | 9/2004 | Singhal et al. |
| 2004/0176817 A1 | 9/2004 | Wahlstrand et al. |
| 2004/0176818 A1 | 9/2004 | Wahlstrand et al. |
| 2004/0176819 A1 | 9/2004 | Wahlstrand et al. |
| 2004/0181263 A1 | 9/2004 | Balzer et al. |
| 2004/0186528 A1 | 9/2004 | Ries et al. |
| 2004/0243481 A1 | 12/2004 | Bradbury et al. |
| 2005/0003268 A1 | 1/2005 | Scott et al. |
| 2005/0004618 A1 | 1/2005 | Scott et al. |
| 2005/0004619 A1 | 1/2005 | Wahlstrand et al. |
| 2005/0004620 A1 | 1/2005 | Singhal et al. |
| 2005/0004637 A1 | 1/2005 | Singhal et al. |
| 2005/0033378 A1 | 2/2005 | Sheffield et al. |
| 2005/0070781 A1 | 3/2005 | Dawant et al. |
| 2005/0070971 A1 | 3/2005 | Fowler et al. |
| 2005/0075679 A1 | 4/2005 | Gliner et al. |
| 2005/0159792 A1 | 7/2005 | Ridder |
| 2005/0228249 A1 * | 10/2005 | Boling ........................ 600/378 |
| 2005/0245806 A1 | 11/2005 | Singhal et al. |
| 2005/0245984 A1 | 11/2005 | Singhal et al. |
| 2006/0004422 A1 | 1/2006 | De Ridder |
| 2006/0094951 A1 | 5/2006 | Dean et al. |
| 2006/0116743 A1 | 6/2006 | Gibson et al. |
| 2006/0129205 A1 | 6/2006 | Boveja et al. |
| 2006/0173510 A1 | 8/2006 | Besio et al. |
| 2006/0184210 A1 | 8/2006 | Singhal et al. |
| 2006/0184220 A1 | 8/2006 | Singhal et al. |
| 2006/0195156 A1 | 8/2006 | Singhal et al. |
| 2007/0074732 A1 | 4/2007 | Singhal et al. |
| 2007/0118243 A1 | 5/2007 | Schroeder et al. |
| 2007/0185539 A1 | 8/2007 | Singhal et al. |
| 2007/0255338 A1 | 11/2007 | Wahlstrand et al. |
| 2008/0021511 A1 | 1/2008 | Scott et al. |
| 2008/0065173 A1 | 3/2008 | Wahlstrand et al. |
| 2009/0281623 A1 | 11/2009 | Kast et al. |
| 2009/0292327 A1 | 11/2009 | Singhal et al. |
| 2009/0299164 A1 * | 12/2009 | Singhal et al. ............... 600/377 |
| 2009/0299165 A1 * | 12/2009 | Singhal et al. ............... 600/377 |
| 2009/0299380 A1 | 12/2009 | Singhal et al. |

FOREIGN PATENT DOCUMENTS

| | | |
|---|---|---|
| EP | 1 145 735 A2 | 10/2001 |
| EP | 1 145 736 A2 | 10/2001 |
| GB | 1 161 579 | 8/1969 |
| WO | WO 92/20402 | 11/1992 |
| WO | WO 99/06108 | 2/1999 |
| WO | WO 99/34758 | 7/1999 |
| WO | WO 00/13743 | 3/2000 |
| WO | WO 00/40295 | 7/2000 |
| WO | WO 01/10369 | 2/2001 |
| WO | WO 01/28622 | 4/2001 |
| WO | WO 01/39830 | 6/2001 |
| WO | WO 01/60450 | 8/2001 |
| WO | WO 01/97906 | 12/2001 |
| WO | WO 02/05590 | 1/2002 |
| WO | WO 02/056637 | 7/2002 |
| WO | WO 02/083207 | 10/2002 |
| WO | WO 02/083208 | 10/2002 |
| WO | WO 02/083233 | 10/2002 |
| WO | WO 03/026739 | 4/2003 |
| WO | WO 03/076012 | 9/2003 |
| WO | WO 2004/043536 | 5/2004 |
| WO | 2004/052459 A1 | 6/2004 |

OTHER PUBLICATIONS

U.S. Appl. No. 12/538,617, filed Aug. 10, 2009, entitled "Implantation of Implantable Medical Device," by Singhal et al.
U.S. Appl. No. 12/609,957, filed Oct. 30, 2009, entitled "Non-Hermetic Direct Current Interconnect," by Wahlstrand et al.
"Surgical Process," Animation Screenshots from http://www.cochleramerica.com/800.asp, 7 pgs. (last printed Feb. 3, 2004).
"Candidates Brochure," http://www.cochleramerica.com/pdfs/candidatebrochglobal.pdf, 14 pgs. (Aug. 19, 2002).
"Research and Development," http;//www.cochlearamericas.com/384.asp, 1 pg. (last printed Feb. 3, 2004).
"The World Leader in cochlear implants—revolutionizing hearing for adults and infants," http://www.cochlear.com, 1 pg. (last printed Feb. 3, 2004).
"Cochlear: innovator of the Nucleus 3 cochlear implant system," http.://www.cochlearamericas.com, 1 pg. (last printed Feb. 3, 2004).
"What is a Cochlear Implant," http://www.cochlearamericas.com/What/161.asp, 1 pg. (last printed Feb. 3, 2004).
"ESPrit 3G Speech Processor," http://www.cochlearamericas.com/591.asp, 2 pgs. (last printed Feb. 3, 2004).
"Nucleus 3 System," http://www.cochlearamericas.com/Products/465.asp, 1 pg. (last printed Feb. 3, 2004).
"Internal Components: Nucleus 24 Cochlear Implants," http://www.cochlearamericas.com/374.asp, 1 pg. (last printed Feb. 3, 2004).
"Nucleus 24 Contour," http://www.cochlearamericas.com/568.asp, 2 pgs. (last printed Feb. 3, 2004).
"Nucleus 24 M," http://www.cochlearamericas.com/372.asp, 1 pg. (last printed Feb. 3, 2004).
"Nucleus 24 K," http://www.cochlearamericas.com/371.asp, 1 pg. (last printed Feb. 3, 2004).
"Nucleus 24 Double Array," http://www.cochlearamericas.com/370.asp, 1 pg. (last printed Feb. 3, 2004).
"Nucleus 24 ABI: Auditory Brainstem Implant," http://www.cochlearamericas.com/373.asp, 2 pgs. (last printed Feb. 3, 2004).
"Nucleus Speech Processors," http://www.cochlearamericas.com/629.asp, 1 pg. (last printed Feb. 3, 2004).
"Sprint: body worn speech processor," http://www.cochlearamericas.com/1010.asp, 1 pg. (last printed Feb. 3, 2004).
"Cochlear," http://www.cochlearamericas.com/Recipients/978.asp, 3 pgs. (last printed Feb. 3, 2004).
Answers.com, www.answers.com, defined: discrete components, acessed on Mar. 2, 2007 (2 pages).

Amendment from U.S. Appl. No. 12/538,623 dated Jan. 31, 2011 (24 pages).
Amendment from U.S. Appl. No. 12/538,617 dated Jan. 31, 2011 (20 pages).
Office Action from U.S. Appl. No. 12/538,617 dated Oct. 29, 2010 (23 pages).
Office Action from U.S. Appl. No. 12/538,623 dated Oct. 29, 2010 (25 pages).
Final Office Action for U.S. Appl. No. 12/538,617 dated Mar. 24, 2011 (22 pages).
Response to Final Office Action for U.S. Appl. No. 12/538,617, filed May 24, 2011 (12 pages).
Advisory Action for U.S. Appl. No. 12/538,617 dated Jun. 9, 2011 (3 pages).
Final Office Action for U.S. Appl. No. 12/538,623 dated Mar. 24, 2011 (25 pages).
Response to Final Office Action for U.S. Appl. No. 12/538,623, filed May 24, 2011 (13 pages).
Advisory Action for U.S. Appl. No. 12/538,623 dated Jun. 10, 2011 (3 pages).
Amendment in response to Office Action dated Jan. 19, 2012 from U.S. Appl. No. 12/119,044, filed on Apr. 13, 2012 (10 pages).
Office Action from related U.S. Appl. No. 12/119,044 dated Jan. 19, 2012 8 pages.
Office Action from U.S. Appl. No. 12/119,044 dated Jul. 19, 2012 (10 pages).

* cited by examiner

EVALUATION OF IMPLANTATION SITE FOR IMPLANTATION OF IMPLANTABLE MEDICAL DEVICE

This application is a divisional of and claims priority to U.S. patent application Ser. No. 10/835,527, filed Apr. 29, 2004, issued as U.S. Pat. No. 7,596,399, the entire content of which is incorporated herein by reference.

TECHNICAL FIELD

The invention relates to implantation and removal of medical devices, and more particularly, to implantable medical devices that deliver therapy to and/or monitor a patient.

BACKGROUND

Implantable medical devices (IMDs) include devices implantable in a mammalian body that sense medical parameters, monitor medical conditions, administer therapy, or any combination thereof. Typical IMDs include a variety of electrical and/or mechanical components, often including a housing that houses the components. Because the components may be fragile, the housing is usually sufficiently robust to protect the components from forces to which they would otherwise be exposed when implanted within the body. Housings may be constructed from titanium, for example. In order to avoid potentially harmful interactions between the components and bodily fluids, such as corrosion, IMD housings are typically hermetically sealed.

Large components common to most IMDs typically include a battery, a coil, and a hybrid circuit that includes digital circuits, e.g., integrated circuit chips and/or a microprocessor, and analog circuit components. IMDs may include other components as well. The components and the housing each add bulk to the IMD.

Some medical devices may be implanted in the head of a patient. For example, an IMD may be implanted under the scalp and on top of the cranium, with one or more leads deployed on the head or implanted in the brain. In many cases, the implantation is not permanent, and it may be advantageous to remove the device for reasons such as repair, maintenance, replacement, or because the patient no longer benefits from the device.

SUMMARY

In general, the invention is directed to techniques for planning and carrying out implantation of an IMD under the scalp of a patient and on top of the patient's skull. Implantation of a cranially implanted IMD includes making an incision in the scalp of a head of a patient to obtain access to the implantation site and implanting the IMD.

The invention addresses strategies that make implantation more efficient and improve the chances of success. Generally speaking, data are collected prior to surgery that assist the surgeon in planning and executing the surgery. The collected data can pertain to the contours of the skull of the patient, the condition of the scalp of the patient, the vascular structure or neurological structures in the head of the patient, and the like. The data may be in the form of images, such as images generated by X-ray, magnetic resonance imaging, CT-scan and fluoroscopy. The data can also be in the form of physical or virtual models of the patient's skull and the IMD.

A surgeon can use the collected data to determine, for example, whether the patient is a candidate for a cranial implantation, and whether the patient's skull and scalp can support the implantation. The surgeon can also determine where the device should be implanted, and how the surgical incisions should be made.

In addition, the surgeon can use the data to determine what configuration of device should be implanted. The IMDs can incorporate a modular design, and the modules may be arranged in a plurality of standard configurations. In other words, IMDs need not be built from scratch for every patient. Rather, the surgeon can select a suitable standard configuration and adapt that configuration to the patient by bending, trimming or otherwise adjusting the IMD to fit the patient. Use of one or more standard configurations is generally more efficient, convenient and economical than building custom IMDs from scratch for each patient.

In one embodiment, the invention is directed to a method comprising receiving an image of a head of a patient and determining, as a function of the image, whether the patient is a candidate for implantation of an implantable medical device between a scalp and a skull. The IMD includes at least one module that includes control electronics within a housing, and is configured to be implanted between the scalp and the skull of the patient. The IMD may also have member that at least partially encapsulates the housing. The method may further include determining whether the patient is a candidate for implantation of the IMD deployed in a recess created in the skull.

In another embodiment, the invention is directed to a method that includes receiving an image of a head of a patient, generating a model of the patient's skull as a function of the image, and providing an implantable medical device configured to be implanted between a scalp and the skull of the patient as a function of the model of the skull. The model of the skull may be a physical model or a virtual model simulated in a computer.

In a further embodiment, the invention presents a method comprising receiving an image of a head of a patient and selecting, from a plurality of configurations of an implantable medical device configured to be implanted between a scalp and a skull, a configuration of the implantable medical device as a function of the image.

In an additional embodiment, the invention is directed to a method that includes receiving an image of a scalp of a patient. The method also includes determining, as a function of the image, whether the patient is a candidate for implantation of an implantable medical device between the scalp and a skull. The method can include conditioning the scalp for implantation of the IMD.

In another embodiment, the invention is directed to a method comprising receiving skull contour data associated with the skull of a patient, and selecting, as a function of the skull contour data, an implantation site for an implantable medical device.

In an added embodiment, the invention is directed to a method that includes receiving a soft-tissue image of a head of a patient, identifying physiological structures in the image, and selecting an incision site as a function of the physiological structures.

In additional embodiments, the invention is directed to methods that include receiving an image of a head of a patient, the image comprising a soft-tissue image and a hard-tissue image, of a head of a patient. In one embodiment, the invention includes receiving an implantation criterion and proposing at least one implantation site for an implantable medical device as a function of the image and the implantation criterion. In another embodiment, the invention includes receiving an implantation site for an implantable medical device, and disclosing to a user information about at least one feature of the head at the implantation site.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
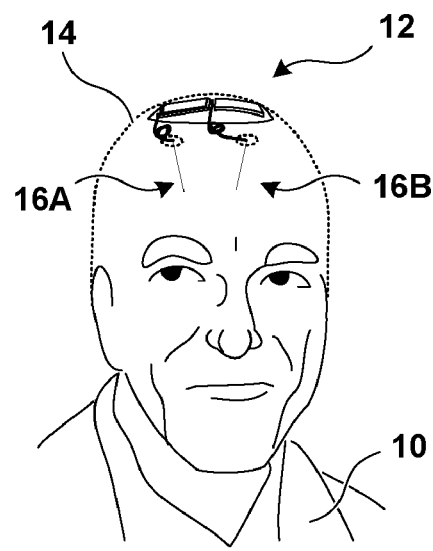
FIG. 1 is a conceptual diagram illustrating deployment of a low-profile IMD under the scalp of a patient.

FIG. 1 shows a patient 10 with a low-profile IMD 12 deployed beneath his scalp 14. In FIG. 1, IMD 12 is a neurostimulator that provides deep brain stimulation via leads 16A, 16B deployed in the brain of patient 10. In the example of FIG. 1, IMD 12 is deployed in proximity to site of stimulation therapy. IMD 12 may be used to treat any nervous system disorder including, but not limited to, epilepsy, pain, psychological disorders including mood and anxiety disorders, movement disorders (MVD) such as, but not limited to, essential tremor and Parkinson's disease and neurodegenerative disorders.

Although IMD 12 is depicted as a neurostimulator, the invention is not limited to applications in which the IMD is a neurostimulator. The invention may be employed with IMDs that perform any monitoring or therapeutic functions. The invention is not limited to IMDs that include leads deployed in the brain, but may also be employed with leads deployed anywhere in the head or neck including, for example, leads deployed on or near the surface of the skull, leads deployed beneath the skull such as near or on the dura mater, leads placed adjacent cranial or other nerves in the neck or head, or leads placed directly on the surface of the brain. Nor is the invention limited to IMDs that are coupled to electrodes. The invention may be employed with low-profile IMDs coupled to any sensing or therapeutic elements, such as temperature sensors or motion sensors. The invention may also be employed with different types of IMDs including, but not limited to, IMDs operating in an open loop mode (also referred to as non-responsive operation), IMDs operating in a closed loop mode (also referred to as responsive), and IMDs for providing monitoring and/or warning.

In the example of FIG. 1, IMD 12 is deployed beneath scalp 14 of patient 10, but on top of the cranium of patient 10. The invention may be applied to other types of implantation as well, such as implantation of IMD 12 in a trough cut into the cranium of patient 10.

Figure 2:
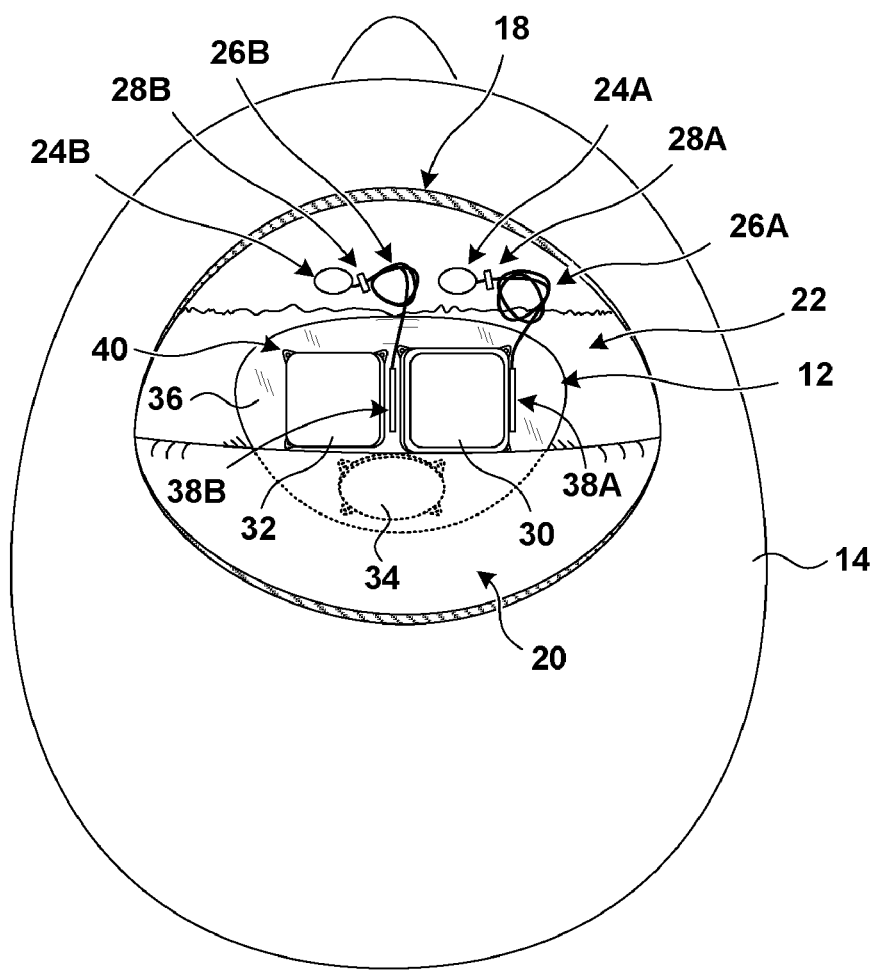
FIG. 2 is a plan diagram of the top of a head of a patient, illustrating an exemplary implantation of a low-profile IMD.

FIG. 2 illustrates a typical implantation of IMD 12 shown in FIG. 1. In a typical implantation, the surgeon makes an incision 18 through the scalp 14 of patient 10, and pulls back the resulting flap of skin 20 to expose the desired area of the cranium 22. The incision may be a "C-flap" incision, for example. Patient 10 may be under local anesthetic. The surgeon drills holes, called "burr holes," in the cranium and deploys leads 16 through the burr holes into the brain.

The surgeon typically places caps 24A and 24B, called "burr hole caps," over the burr holes. A portion of the bodies of leads 16A and 16B, identified with reference numerals 26A and 26B, is deployed outside of the brain on the surface of skull 22. Before connecting leads 26A and 26B to IMD 12, the surgeon typically "manages" the leads. Lead management includes arranging the excess length of leads 16 using techniques such as coiling and anchoring with anchoring plates. In a typical implantation, the surgeon arranges the leads to provide some slack to reduce the risk of lead migration. In FIG. 2, leads 26A and 26B are depicted as coiled, and are anchored by anchoring plates 28A and 28B.

The surgeon implants IMD 12 between scalp 14 and skull 22. In one surgical procedure, the surgeon uses a tool to form a pocket beneath scalp 14 proximate to the burr holes, and positions IMD 12 in the pocket. The surgeon may fix IMD 12 to the cranium using an attachment mechanism such as bone screws. The surgeon closes skin flap 20 over IMD 12, and then staples or sutures the incision.

In FIG. 2, IMD 12 is a low-profile device, allowing it to be implanted between scalp 14 and skull 22, with little discomfort or adverse cosmetic consequences to patient 10. A low-profile IMD also typically lacks high protrusions with sharp corners that could cause skin erosion. IMD 12 comprises one or more modules that carry out the various functions of IMD 12. As shown in FIG. 2, IMD 12 includes at least three modules: a control module 30, a power supply module 32 and a recharge module 34. One or more of modules 30, 32, 34 includes a housing that can carry out a variety of functions, including encasing the components of the modules, sealing the modules against contamination, electrically isolating electrical components, and the like. The modules are coupled to a member 36, which may be made of a soft, biocompatible material. Member 36 at least partially encapsulates one or more housings of modules 30, 32, 34, and generally serves as a smooth interface between the modules and the body tissue. Leads 26A and 26B are coupled to IMD 12 at lead connectors 38A and 38B. IMD 12 may be anchored with an anchoring mechanism such as a metallic tab 40 that includes an opening for receiving a bone screw.

In general, member 36 integrates modules 30, 32 and 34 into a desired form factor, but, where flexible, allows relative intermodule motion. In some embodiments, member 36 incorporates mechanical features to restrict intermodule motion to certain directions or within certain ranges. Member 36 may be made from silicone, and is some embodiments may be made from two or more materials of differing flexibility, such as silicone and a polyurethane. An exemplary polyurethane for this purpose is Tecothane®, which is commercially available from Hermedics Polymer Products, Wilmington, Mass. Member 36 may also be referred to as an "overmold," but use of the term "overmold" herein is not intended to limit the invention to embodiments in which member 36 is a molded structure. Member 36 may be a molded structure, or may be a structure formed by any process.

The invention is not limited to the particular IMD depicted in FIG. 2, but includes a number of embodiments, some of which are described in more detail below.

Figure 3:
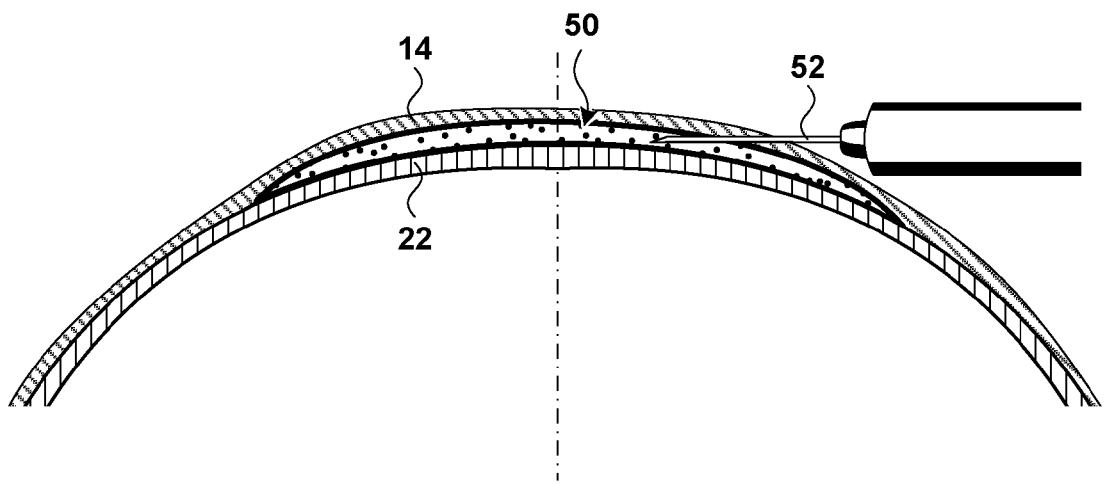
FIG. 3 is a cross-sectional diagram of an implantable conditioning device implanted between the scalp and skull of a patient, and illustrating a technique for adding fluid to the implantable conditioning device.

FIG. 3 is a cross-sectional view of the top of the head of a patient, and illustrates an embodiment of the invention. In some cases, scalp 14 may not be sufficiently elastic to close over IMD 12. Patient 10 may benefit from having the scalp stretched or conditioned prior to implantation of IMD 12. Stretching of the scalp can contribute to patient comfort, for example, as well as easier closure of the incision following implantation, along with attendant benefits such as a reduced risk of infection. Implantation of a dummy IMD 50 prior to implantation of working IMD 12 can help condition scalp 14.

A surgeon may implant dummy IMD 50 in a manner similar to implantation of a working IMD. For example, the surgeon may make a C-flap incision as shown in FIG. 2, and pull back the scalp flap to expose the skull. The surgeon may further separate a part of the scalp from the skull to create a pocket, and place at least a portion of dummy IMD 50 in the pocket. The surgeon covers at least a portion of dummy IMD 50 with the scalp flap and sutures the scalp flap to close the incision.

As illustrated in FIG. 3, dummy IMD 50 need not provide sensing or therapy. Rather, dummy IMD 50 is a device that is comparable in dimension to working IMD 12 (not shown in FIG. 3). In FIG. 3, dummy IMD 50 is implanted between scalp 14 and cranium 22, and covers about as much surface area of cranium 22 as would be covered by working IMD 12. In one embodiment, dummy IMD 50 is at the time of implantation thinner than working IMD 12. The thinness of dummy IMD 50 enables the surgeon to close the incision in scalp 14 more easily.

Dummy IMD 50 may be formed from any number of biocompatible materials. In a typical embodiment, dummy IMD 50 is formed from a soft, pliable and fluid-tight polymer such as silicone.

In the embodiment of the invention shown in FIG. 3, dummy IMD 50 does not have a fixed volume. Rather, dummy IMD 50 comprises an inflatable interior, such as a sac or pouch that can be expanded. The sac may comprise, for example, a self-sealing silicone envelope that can be increasingly filled with a fluid such as saline by injection through the scalp. FIG. 3 depicts an expansion technique, in which a hypodermic needle 52 injects fluid into the interior of dummy IMD 50.

Figure 4:
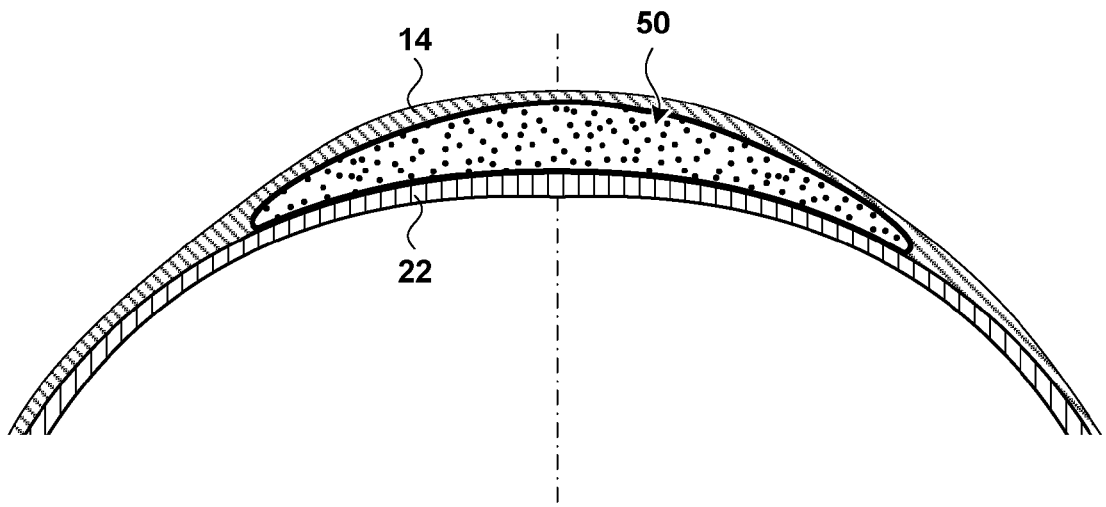
FIG. 4 is a cross-sectional diagram of the implantable conditioning device shown in FIG. 4, following the addition of fluid.

FIG. 4 shows dummy IMD 50 with an expanded volume. In FIG. 4, the volume or profile of dummy IMD 50 may be comparable to the volume or profile of working IMD 12. Increased quantities of fluid may have been injected into dummy IMD 50 over time, causing scalp 14 to stretch gradually. The time for scalp conditioning may vary from patient to patient, but stretching may take place over about two weeks, in a typical patient. Gradual stretching of scalp 14 with expandable dummy IMD 50 may effectively pre-condition scalp 14 for the implantation of working IMD 12.

Figure 5:
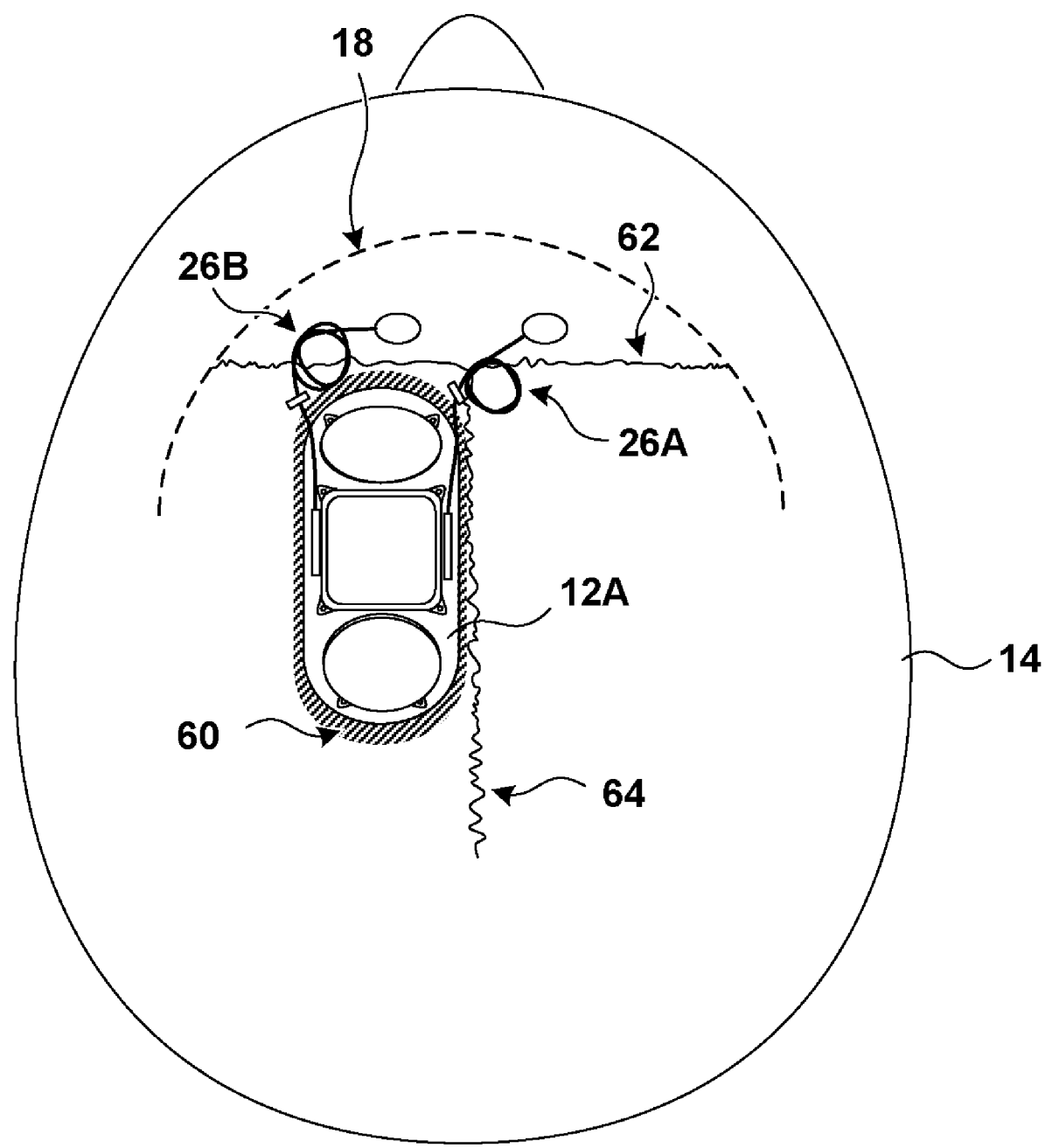
FIG. 5 is a plan diagram of the top of a head of a patient, illustrating an exemplary implantation of a low-profile IMD in a trough.

FIG. 5 is a conceptual imaging diagram of the top of a head of a patient, with the scalp being invisible for clarity. FIG. 5 illustrates an exemplary implantation technique. In FIG. 5, the IMD 12A is a modular implantable device with a soft, biocompatible member, similar to IMD 12. Unlike IMD 12, the modules of IMD 12A are deployed in a linear rather than a triangular configuration.

In FIG. 5, the surgeon has made incision 18 and has deployed leads 26A and 26B. The surgeon has also prepared a pocket between the scalp and the skull for deployment of IMD 12A. Prior to deployment of IMD 12A, however, the surgeon created a trough or recess 60 in the skull to receive the IMD 12A. When recess 60 receives IMD 12A, and the scalp is closed, IMD 12A is implanted between the scalp and the skull. By deploying IMD 12A inside recess 60, IMD 12A can have an external appearance of a smaller profile. In other words, IMD 12A may be result in less bulging on the patient's head. The low profile can have cosmetic benefit, and can also be advantageous to patients that have less elastic scalps.

In FIG. 5, the surgeon gouges recess 60 posterior to the coronal suture 62, and proximate to the sagittal suture 64 of skull 22. Such recess positioning and IMD deployment are for purposes of illustration, and the invention supports other recess positions or IMDs.

Figure 6:
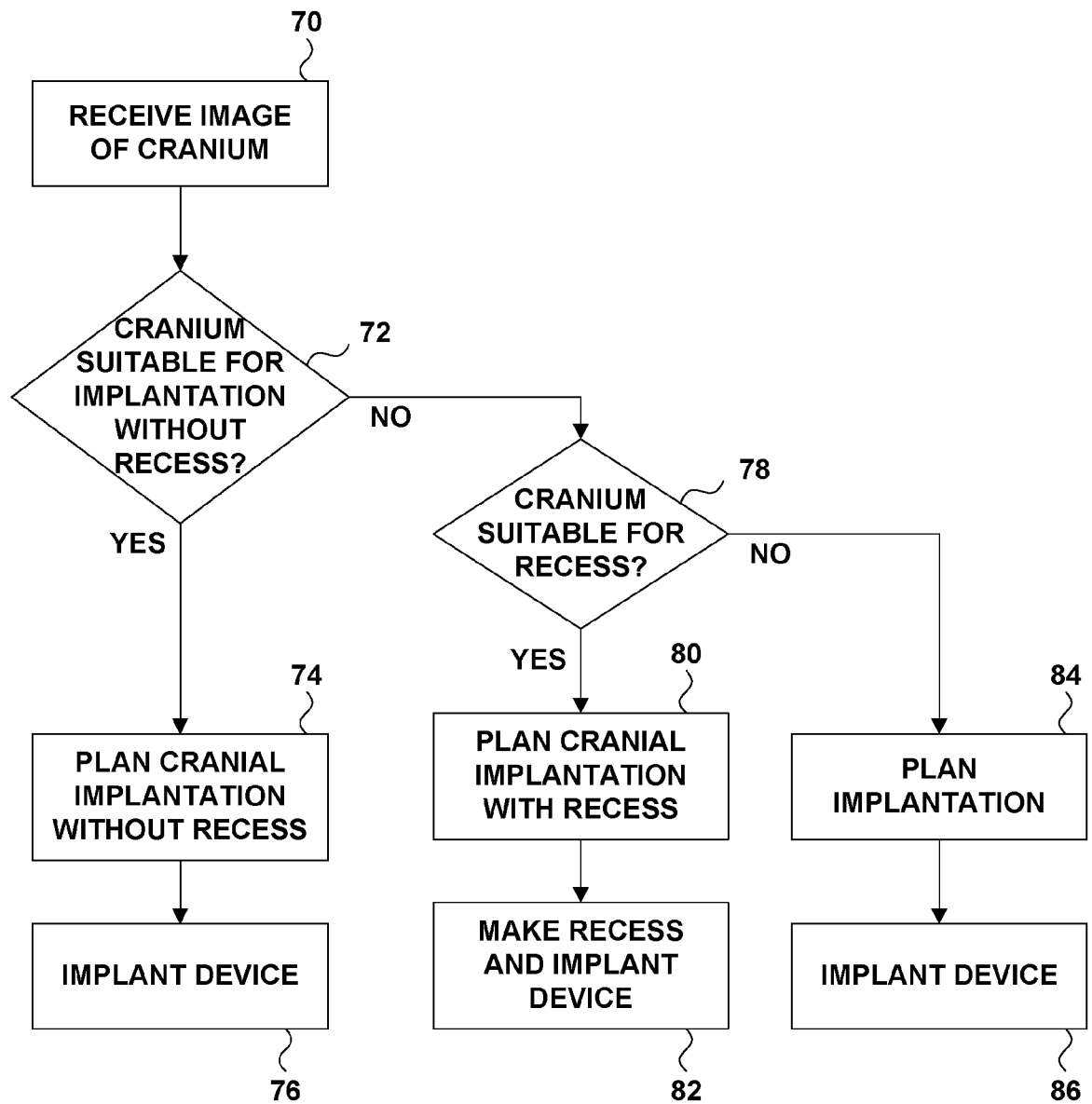
FIG. 6 is a flow diagram illustrating a technique for identifying potential locations and implantation strategies for an implanted low-profile IMD.

FIG. 6 is a flow diagram illustrating a technique for identifying potential locations and implantation strategies for an implanted low-profile IMD. Before implanting the implanted device, the surgeon should ordinarily make a determination about what site is appropriate for the patient. Accordingly, the surgeon may direct that the patient be imaged using one or more medical imaging techniques such as X-ray, magnetic resonance imaging (MRI), CT-scan or fluoroscopy. The surgeon receives the images of the head (70) and identifies potential locations for an implanted low-profile IMD based upon the images.

Before making a cranial implantation with a recess, such as recess 60 depicted in FIG. 5, the surgeon determines whether the patient is a candidate for a cranial implantation, i.e., whether the patient's cranium is suitable for such an implantation. The surgeon considers criteria such as skull curvature, skull thickness, scalp thickness, location of vascular and neurological structures, potential incision locations, and the like. If the patient has a normal skull and scalp, and has no irregularities that would be expected to impede implantation without a recess, then the surgeon can explore cranial implantation without a recess (72) and can plan the implantation accordingly (74). In planning the implantation, the surgeon generally refers to the images to identify implant sites. Thereafter, the surgeon implants the IMD (76).

In some cases, the patient may be a candidate for a cranial implantation with a recess, and the surgeon considers whether a cranial implantation with a recess is indicated (78). When a cranial implantation with a recess is feasible, the surgeon plans the operation based on the images (80) before commencing the operation (82). In some procedures, the recess may be formed by a computer-controlled device that forms the recess in the cranium.

In some cases, the surgeon refers to the images and determines that the patient is not a candidate for cranial implantation. In such cases, the surgeon plans an implantation at another site (84), such as the neck or trunk of the patient, before commencing the operation (86).

Figure 7:
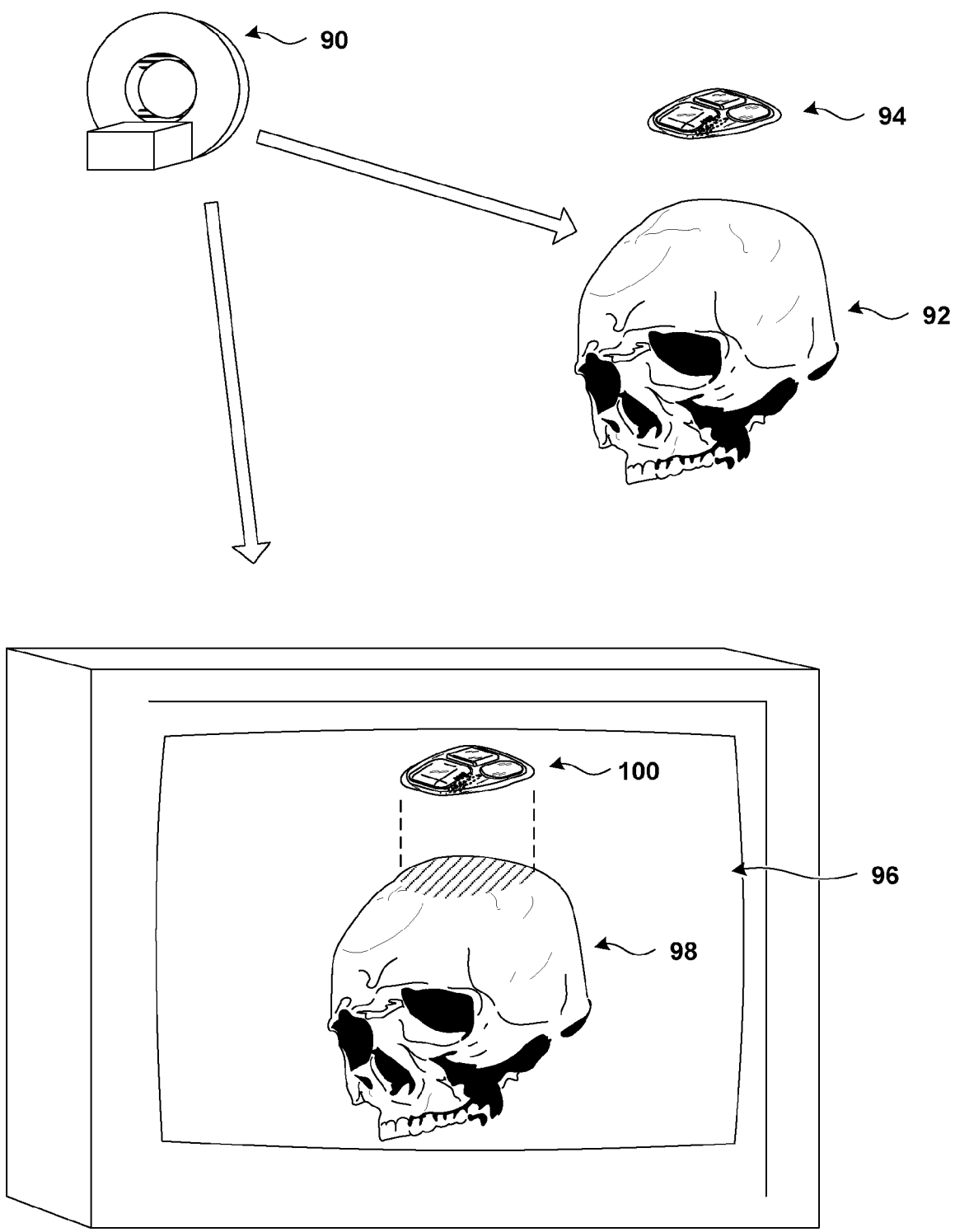
FIG. 7 is a conceptual diagram illustrating use of image data to develop physical or virtual models.

FIG. 7 is a conceptual diagram showing techniques for planning the implantation of an IMD between a scalp and a skull of a patient, based upon images from one or more of the medical imaging techniques mentioned above. One or more pieces of imaging equipment 90 take images of the skull of the patient, resulting in image data. In one embodiment of the invention, a physical model of the patient's skull 92 is constructed with the image data. Physical skull model 92 is a representation of the patient's skull. A physical IMD 94 can then be tailored to conform to physical model 92. Physical IMD 94 may be the actual IMD to be implanted in the patient. By adjusting IMD 94 to fit the model representation of the patient's skull prior to surgery, the actual working IMD can be adjusted to fit the patient's actual skull, reducing the time needed for IMD adjustment during surgery.

In another embodiment of the invention, the image data are supplied to a computer system 96, which generates a virtual model of the patient's skull 98 and a virtual IMD 100. Virtual IMD 100 can be selected from a plurality of virtual IMD configurations, and virtual modeling supports simulating implantation of several virtual IMD configurations. Virtual IMD 100 can then be tailored to conform to virtual skull 98. Once virtual IMD 100 is tailored to virtual skull 98, the dimensions of virtual IMD 100 can be used to construct an actual IMD.

Figure 8:
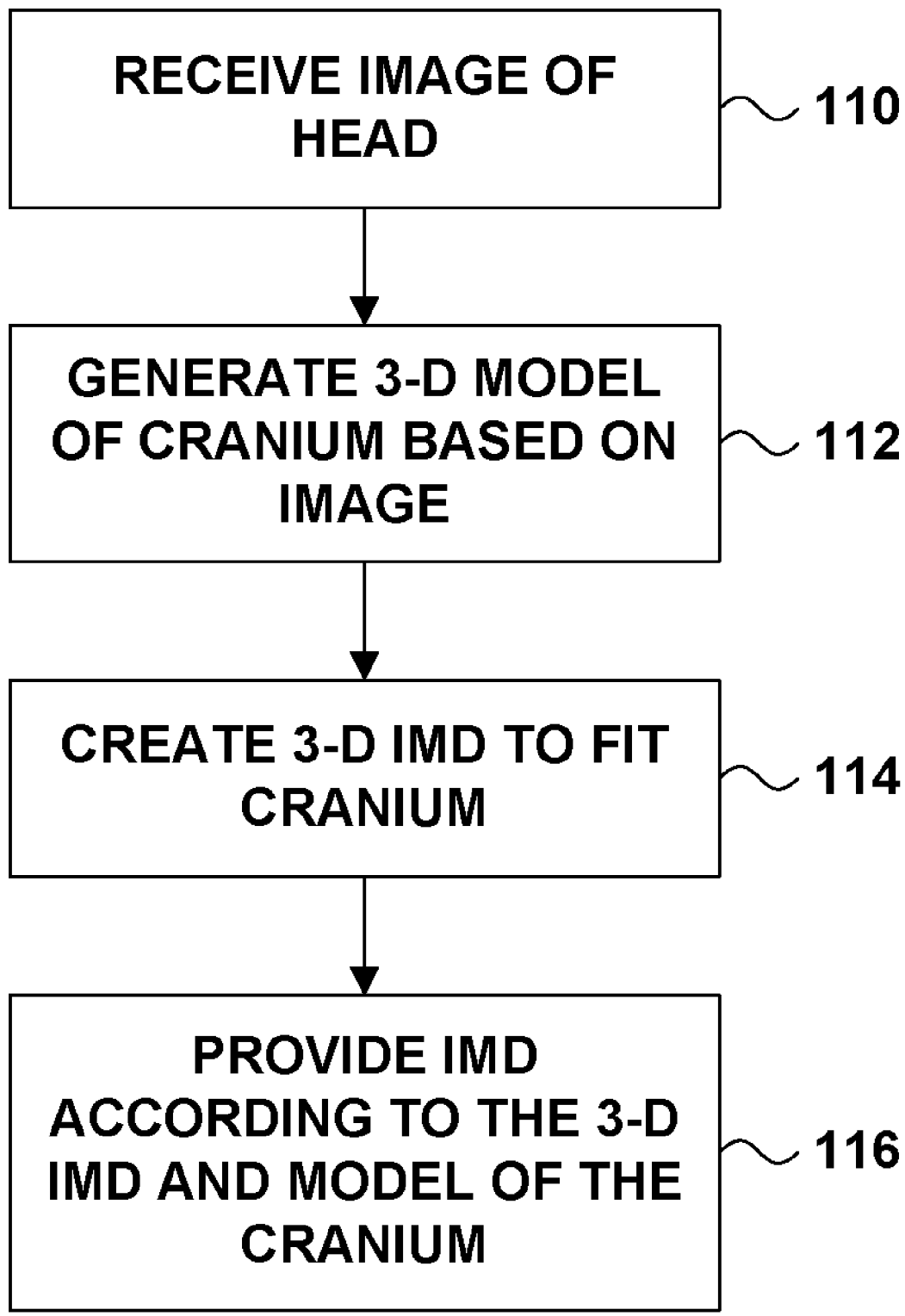
FIG. 8 is a flow diagram further showing the use of image data to develop physical or virtual models, and constructing an IMD based on the models.

FIG. 8 is a flow diagram that summarizes the techniques depicted in FIG. 7. Upon receiving one or more images of the head of a patient (110), a model-maker generates a three-dimensional model of the cranium based on the images (112). The model can be a physical model or a virtual model. Thereafter, a physical or virtual three-dimensional IMD can be created to fit the model of the cranium (114), and a working IMD can be constructed, adapted or otherwise provided, according to the three-dimensional IMD and the model of the cranium (116). When the three-dimensional model of the cranium is a physical model, the actual IMD selected for implantation can be modified to fit the physical model of the skull. In the case of a virtual IMD, the physical IMD is provided as a function of the virtual IMD.

In some cases, providing the IMD comprises making adjustments to a standard IMD or to one of a set of standard IMDs to meet the needs to the patient. In other cases, providing the IMD comprises constructing a customized IMD for the patient.

Employment of modeling techniques prior to surgery can result in many advantages for the patient. Modeling can help the surgeon select an implantation site, and can help the surgeon select a recess location, if suitable. Modeling can further help the surgeon select a configuration of modules. A triangular configuration of modules, such as depicted in FIG. 2, may be appropriate for one patient's skull, while a linear configuration, such as depicted in FIG. 5, may be appropriate for another patient's skull.

An advantage of modular IMDs such as those depicted in FIGS. 2 and 5 is that a standard configuration of an IMD can be adapted to a patient, without having to build the IMD from scratch and without having to customize every component of the IMD. The surgeon may select any from several standard configurations of standard modules. Accordingly, construction of the IMD (116) can comprise making adjustments to a standard IMD so that the IMD will better fit the patient. Adjusting the IMD can include bending the IMD, positioning the modules of the IMD, trimming the IMD, and the like.

Figure 9:
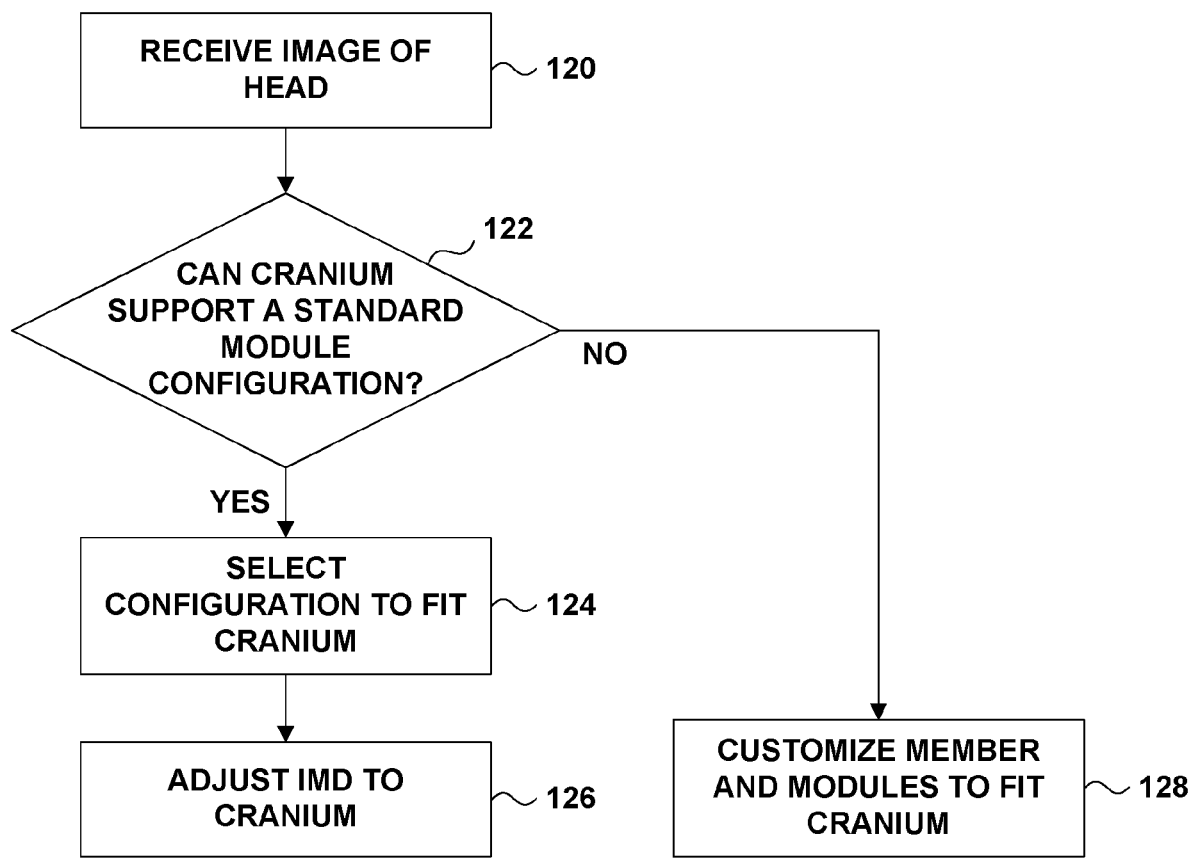
FIG. 9 is a flow diagram illustrating the use of image data to select an IMD for implantation in a patient.

FIG. 9 is a flow diagram illustrating the use of image data of the head of a patient to select an IMD configuration. Upon receiving image data (120), the surgeon determines whether the patient can use a standard module configuration, or whether the patient would benefit from a fully customized IMD (122). The surgeon uses the image data, which may be incorporated into physical or virtual models of the cranium, to determine whether one or more standard configurations are suitable for the patient. The image data can include information pertaining to criteria such as skull curvature, skull thickness, scalp thickness, location of vascular and neurological structures, potential incision locations, and the like. The surgeon may select a configuration (124) and may adjust the IMD to the cranium of the particular patient (126).

It is generally more efficient, convenient and economical to employ a standard configuration of IMD that is adjusted to the patient, than to build an IMD from scratch that is fully customized for the patient. Thus, it can be advantageous for the surgeon to select a particular IMD from a plurality of standard IMD configurations. In the event the surgeon determines that the patient cannot benefit from a standard module configuration, however, the surgeon may direct the creation of a customized IMD (128).

Figure 10:
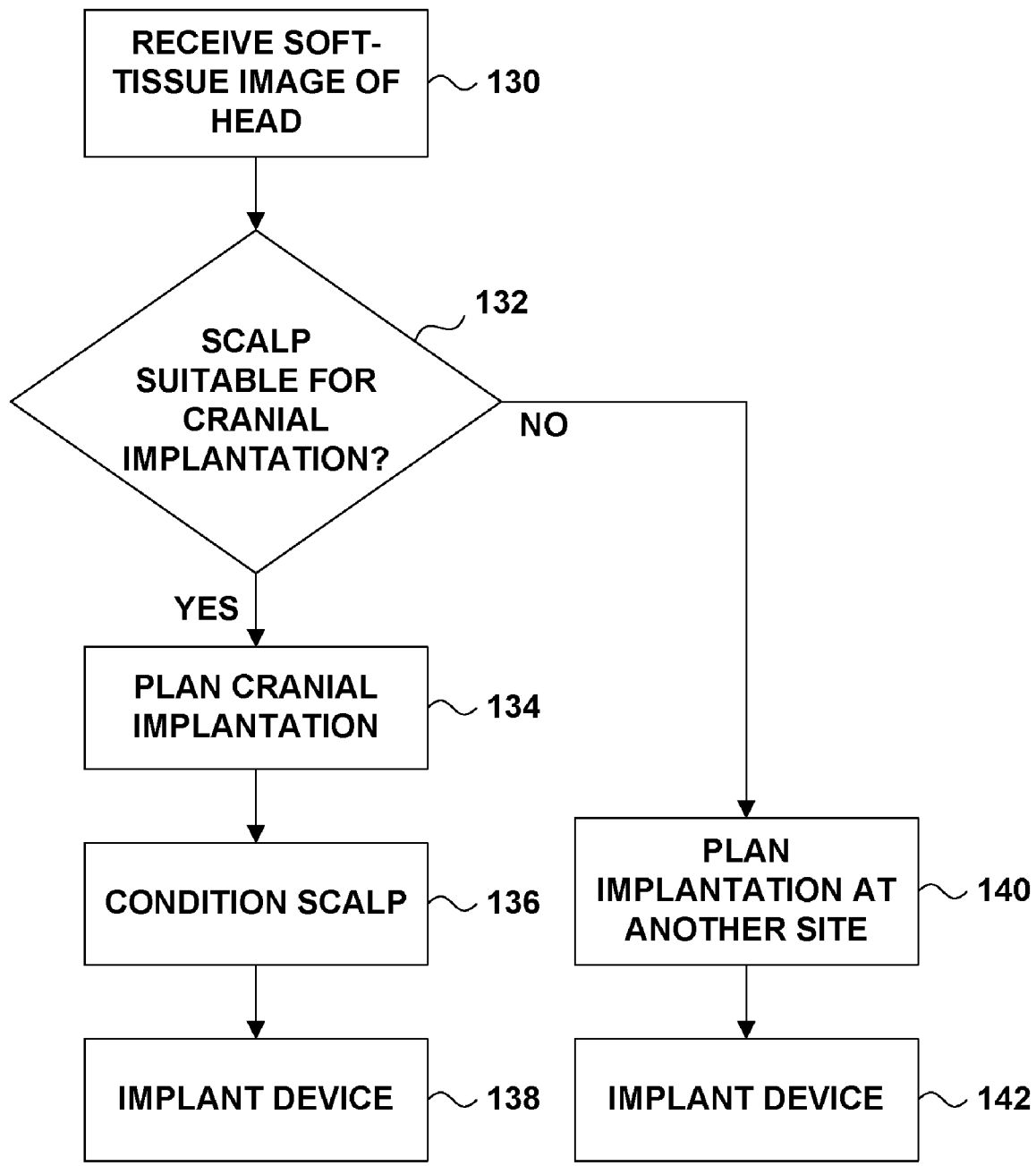
FIG. 10 is a flow diagram illustrating selection of an implantation site for an IMD based upon image data showing the patient's scalp.

FIG. 10 is a flow diagram illustrating the use of image data showing the scalp to select an implantation site for an IMD. A cranial implantation may be desirable, but soft-tissue imaging may indicate that the patient's scalp would be unable to support an implantation of an IMD between the scalp and the skull. Soft-tissue imaging can include magnetic resonance imaging or ultrasound imaging, for example.

Accordingly, upon receiving one or more soft-tissue images of the head (130), the surgeon may determine whether the patient's scalp can support a cranial implantation (132), and if so, the surgeon plans a cranial implantation (134). Preparation for cranial implantation (138) may optionally include scalp conditioning (136), such as implantation and expansion of a dummy IMD as depicted in FIGS. 2 and 3. When the patient's scalp cannot support a cranial implantation, the surgeon may plan and carry out implantation at another site (140, 142).

Figure 11:
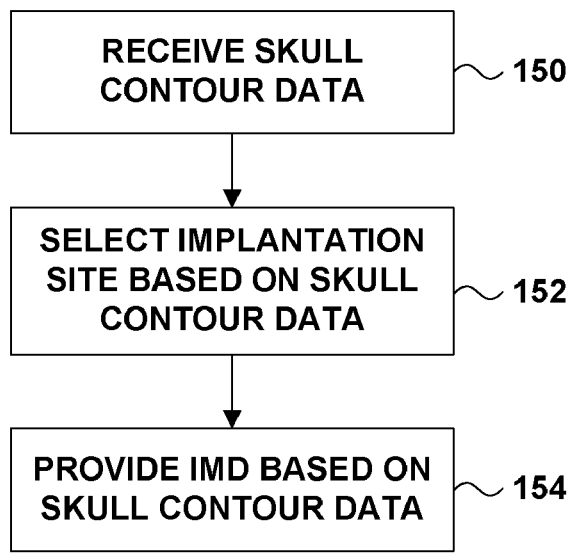
FIG. 11 is a flow diagram showing selection of an implantation site for an IMD as a function of skull contour data

FIG. 11 is a flow diagram illustrating the use of skull contour data to select an implantation site for an IMD. Skull contour data is any data associated with the contour of the patient's skull, and includes, but is not limited to, data obtained from imaging. Skull contour data can also be obtained from gross examination and measurement of the head of the patient. After receiving skull contour data (150), the surgeon selects an implantation site (152). The surgeon can further provide an IMD as a function of the skull contour data (154). Providing the IMD includes, but is not limited to, constructing an IMD and adapting a standard configuration of an IMD to the contours of the patient's skull.

Figure 12:
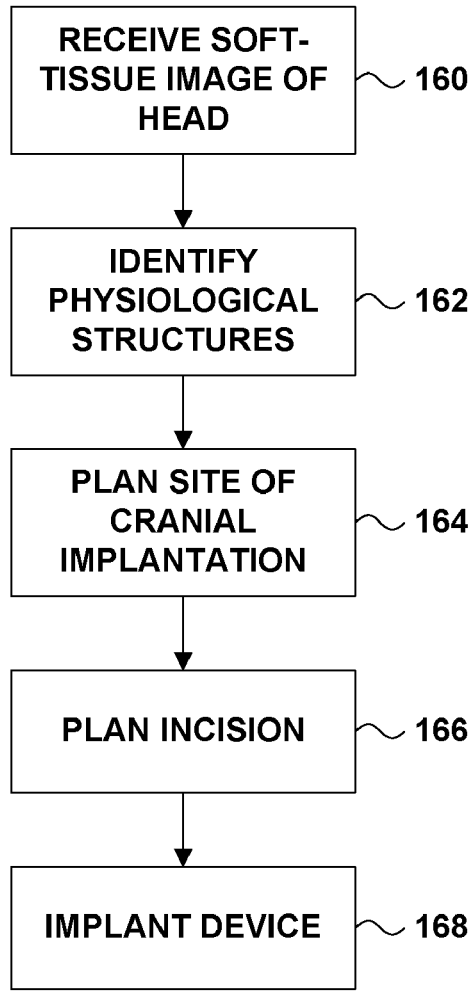
FIG. 12 is a flow diagram illustrating techniques for selection of an implantation site and an implantation strategy based on soft-tissue image data.

FIG. 12 is a flow diagram illustrating the use of soft-tissue image data to select an implantation site for an IMD and an implantation strategy. In some cases, implantation may involve circumstances in which implantation of an IMD between the scalp and the skull may affect physiological structures such as blood vessels or nerves. Although a C-flap incision, such as incision 18 shown in FIG. 2, may have generally predictable vascular and neurological effects, circumstances can arise in which an unconventional incision may be in order. When selecting an incision site, the surgeon ordinarily takes into consideration not only the desired site of implantation, but also potential bleeding and nerve damage that could result from the incision to achieve the implantation.

Accordingly, the surgeon may receive one or more soft-tissue images (160) that include physiological structures such as vascular and neurological structures (162). Using this image data, the surgeon can plan the site of the cranial implantation (164) and can develop an incision strategy (166) to bring about the implantation (168).

Figure 13:
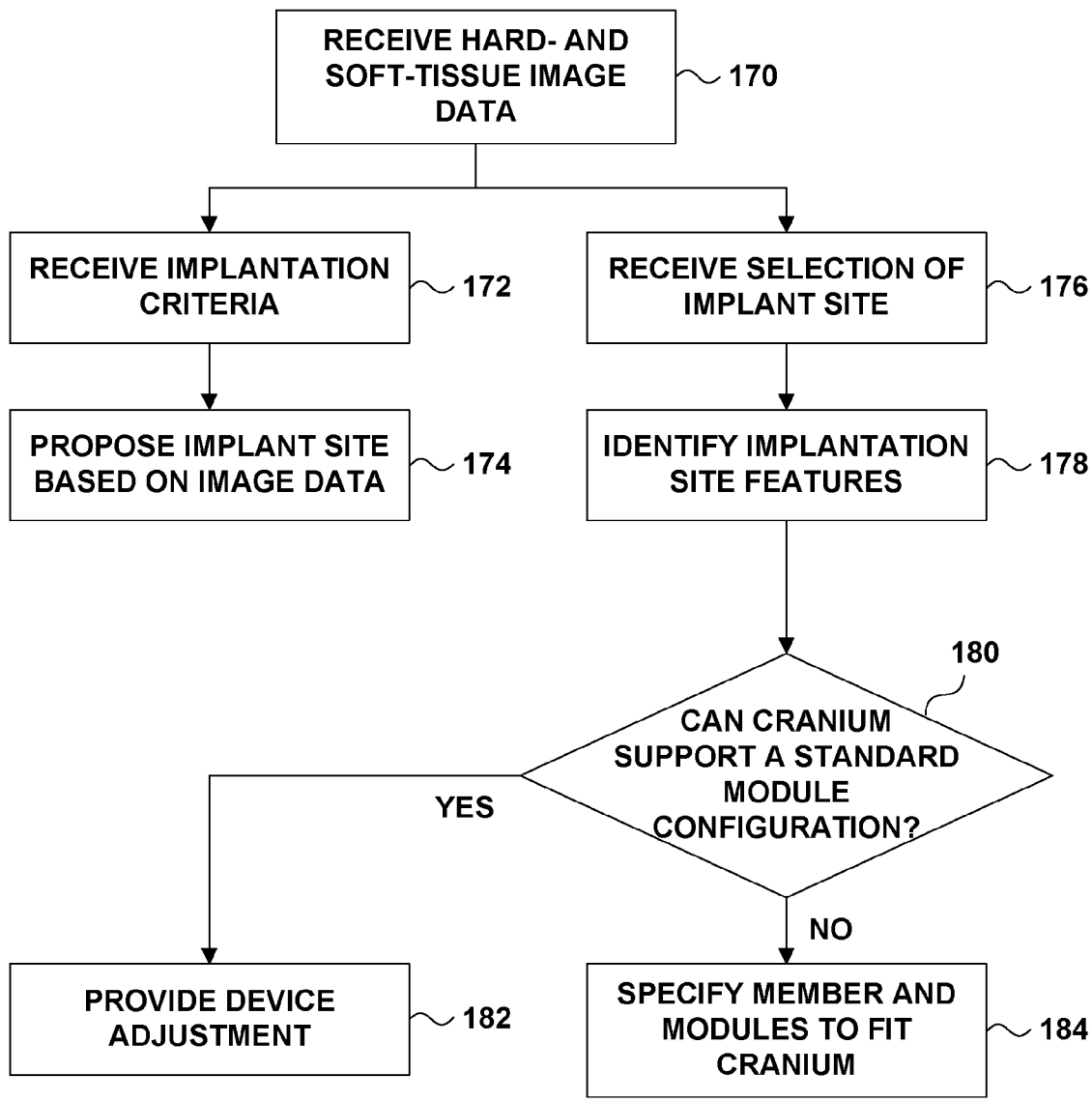
FIG. 13 is a flow diagram illustrating applying the techniques of the invention with an imaging system that uses hard- and soft-tissue image data.

FIG. 13 is a flow diagram illustrating use of hard- and soft-tissue image data to select an implantation site. An imaging system, such as the FrameLink Stereotactic Linking System, produced by and commercially available from Medtronic Surgical Navigation Technologies, can combine hard- and soft-tissue image data to generate a three-dimensional model of an imaged body part, such as the head of the patient. The imaging system integrates hard-tissue data, such as data from an x-ray or CT scan, with soft-tissue data, such as data from an MRI scan.

In the embodiment depicted in FIG. 13, a surgeon uses an imaging system that integrates hard- and soft-tissue image data to select an implantation site. The imaging system receives the hard- and soft-tissue image data (170), and can assist the surgeon along at least two distinct paths. In one path, the imaging system receives the surgeon's implantation criteria (172). The surgeon's implantation criteria pertain to the features of the head or the features of the IMD or both. The surgeon's implantation criteria may include, for example, a range of skull curvatures, a minimum skull thickness, a minimum scalp thickness, a minimum distance from vascular and neurological structures, a planned incision location, and the like. Upon receiving the implantation criteria, the imaging system searches the image for an implantation site that meets the criteria (174).

It is possible that more than one site may satisfy the surgeon's implantation criteria. The imaging system may present the sites in hierarchical order according to any standard, such as closest site to the burr hole caps, site with the greatest scalp thickness, and so forth. In this way, the surgeon can assess her options for implantation. It is also possible the imaging system will find no site that will satisfy all of the surgeon's implantation criteria, and the imaging system may present in any order the sites that come closest to meeting the implantation criteria.

In a variation of this embodiment, the surgeon selects a potential implantation site (176) and the imaging system discloses information to the surgeon about the features of the head at that site (178). Upon receiving the surgeon's selection of a site anterior to the coronal suture of the skull and straddling the sagittal suture of the skull, the imaging system informs the surgeon about skull curvature at the site, skull thickness, scalp thickness, nearby vascular and neurological structures, peaks and valleys of the skull or other anomalies, and so forth. The surgeon may evaluate several potential implantation sites in the same fashion.

Optionally, the imaging system can provide information about a device configuration that will be suitable for a particular implantation site. The imaging system can determine whether a standard configuration of an IMD can be implanted at a particular site (180). In the event the imaging system determines that a standard configuration of an IMD can be implanted at the site, the imaging system can further inform the surgeon how a standard configuration of an IMD can be flexed, bent, trimmed or otherwise adjusted for implantation at the particular site (182). In the event the imaging system determines that a standard configuration of an IMD cannot be adjusted for implantation at the site, the imaging system can specify components or dimensions for a customized IMD (184).

The techniques of FIG. 13 can assist a surgeon who is considering whether to make an implantation with a recess in the skull and can assist the surgeon in finding a recess site. The techniques of FIG. 13 can also assist a surgeon who is considering whether to make a pocket, and can help the surgeon estimate the size of the pocket. The techniques of FIG. 13 can further assist a surgeon in the development of an incision strategy, in the selection of anchor points, in the formation of a lead management strategy, and other practical aspects of the implantation procedure. In addition, the techniques of FIG. 13 can provide information to a surgeon that may help a surgeon determine whether the patient is a candidate for an IMD.

Furthermore, the two paths shown in FIG. 13 are not exclusive of one another. In other words, the imaging system can receive implantation criteria (172) and find one or more possible implantation sites (174), and the surgeon may evaluate each site or nearby sites (176) to learn about the features of the head at each site (178). Similarly, the surgeon can select an implantation site (176), and the imaging system can provide information about the site (178), including information as to whether the site meets received implantation criteria (172). The surgeon can take advantage of one or both paths to select an implantation site.

In a typical embodiment, the imaging system is configured to display the IMD implanted at one or more sites. The invention encompasses embodiments, however, in which an image of the IMD is not incorporated with the hard- and soft-tissue image data.

The invention may also be embodied as a computer-readable medium that includes instructions for causing a programmable processor, such as a processor that processes the hard- and soft-tissue image data, to carry out the methods described above. A "computer-readable medium" includes but is not limited to read-only memory, Flash memory and a magnetic or optical storage medium. The instructions may be implemented as one or more software modules, which may be executed by themselves or in combination with other software.

Although the invention addresses various aspects of surgical strategies, the invention is not limited to the particular considerations described above. The selected site of cranial implantation of an IMD may be a function of factors other than or in addition to the patient's scalp thickness, skull thickness or skull contours. The selected site may be a function of the site of deployment of leads, for example, or the number of leads deployed. The surgeon may also weigh practical considerations pertaining to removal, or explantation, of the IMD after a time. In other words, a surgeon may select an implantation site that can be readily accessed in a future operation to remove the implanted device.

The invention supports implantation of an IMD that performs any of several functions. The invention supports explantation of IMDs that provide monitoring, IMDs that administer therapy, and IMDs that do both. The invention is not limited to any particular number of modules, or any particular arrangement of modules, or to any particular functionality.

Various embodiments of the invention have been described. As mentioned above, the invention is not limited to the particular embodiments described or shown in the figures. These and other embodiments are within the scope of the following claims.

The invention claimed is:

1. A non-transitory computer-readable medium comprising instructions for causing a programmable processor to:
    receive image data representing at least one image of a head of a patient;
    evaluate, as a function of the at least one image, whether an implantation site under a scalp of the patient for a housing of an implantable medical device satisfies an implantation criterion, the implantable medical device including: the housing, control electronics encased within the housing, and a lead coupled to the housing; and
    disclose to a user whether the implantation site for the housing satisfies the implantation criterion;

wherein the instructions to evaluate, as a function of the at least one image, whether the implantation site satisfies the implantation criterion include instructions to identify, based on the at least one image, one or more of skull curvature, skull thickness, scalp thickness, locations of one or more vascular structures within the scalp, or locations of one or more nerves within the scalp, and evaluate whether the implantation site satisfies the implantation criterion based on the one or more of the skull contour, skull thickness, scalp thickness, locations of one or more vascular structures within the scalp, or locations of one or more nerves within the scalp.

2. The medium of claim 1, wherein receiving the at least one image comprises receiving an image generated by at least one of X-ray, magnetic resonance imaging, CT-scan, or fluoroscopy.

3. The medium of claim 1, the instructions further causing the processor to evaluate, as a function of the at least one image, whether the patient is a candidate for implantation of the implantable medical device deployed in a recess created in the skull.

4. The medium of claim 1, the instructions further causing the processor to evaluate, based on the at least one image, whether there are any irregularities in the skull or the scalp of the patient that would impede implantation of the implantable medical device.

5. The medium of claim 1, the instructions further causing the processor to select, from a plurality of configurations of the implantable medical device, one of the configurations of the implantable medical device as a function of the at least one image.

6. The medium of claim 5, wherein the plurality of configurations includes a configuration of at least three modules in a triangular configuration and a configuration of at least two modules in a linear configuration.

7. The medium of claim 5, wherein selecting one of the configurations includes selecting the configuration as a function of one or more of skull contour, skull thickness, scalp thickness, locations of one or more vascular structures, or locations of one or more neurological structures indicated by the at least one image.

8. The medium of claim 1, wherein the at least one image of the head of the patient includes an image of a scalp of the patient.

9. The medium of claim 1, the instructions further causing the processor to:
evaluate skull contour data based on the at least one image of the head;
propose, as a function of the skull contour data, the implantation site for the housing; and
disclose the proposed implantation site to the user.

10. The medium of claim 1, the instructions further causing the processor to:
receive the implantation criterion; and
propose at least the implantation site for the housing based on the implantation criterion and the one or more of the skull contour, skull thickness, scalp thickness, locations of one or more vascular structures within the scalp, or locations of one or more nerves within the scalp.

11. The medium of claim 10, the instructions further causing the processor to:
propose a second implantation site for the housing based on the implantation criterion and the one or more of the skull contour, skull thickness, scalp thickness, locations of one or more vascular structures within the scalp, or locations of one or more nerves within the scalp.

12. The medium of claim 1, wherein the implantation criterion comprises one or more potential incision locations.

13. The medium of claim 1, the instructions further causing the processor to receive an indication of the implantation site from the user.

14. The medium of claim 1, wherein the at least one image of the head of the patient includes a soft-tissue image and a hard-tissue image of the head of the patient.

15. The medium of claim 1, wherein the instructions to evaluate, as a function of the at least one image, whether the implantation site satisfies the implantation criterion include instructions to identify, based on the at least one image, the skull curvature and evaluate whether the implantation site satisfies the implantation criterion based on the skull curvature.

16. The medium of claim 1, wherein the instructions to evaluate, as a function of the at least one image, whether the implantation site satisfies the implantation criterion include instructions to identify, based on the at least one image, the skull thickness and evaluate whether the implantation site satisfies the implantation criterion based on the skull thickness.

17. The medium of claim 1, wherein the instructions to evaluate, as a function of the at least one image, whether the implantation site satisfies the implantation criterion include instructions to identify, based on the at least one image, the scalp thickness and evaluate whether the implantation site satisfies the implantation criterion based on the scalp thickness.

18. The medium of claim 1, wherein the instructions to evaluate, as a function of the at least one image, whether the implantation site satisfies the implantation criterion include instructions to identify, based on the at least one image, the locations of one or more vascular structures within the scalp and evaluate whether the implantation site satisfies the implantation criterion based on the locations of one or more vascular structures within the scalp.

19. The medium of claim 1, wherein the instructions to evaluate, as a function of the at least one image, whether the implantation site satisfies the implantation criterion include instructions to identify, based on the at least one image, the locations of one or more nerves within the scalp and evaluate whether the implantation site satisfies the implantation criterion based on the locations of one or more nerves within the scalp.

20. A method comprising:
receiving, with a computer system, image data representing at least one image of a head of a patient;
evaluating, with the computer system, as a function of the at least one image, whether an implantation site under a scalp of the patient for a housing of an implantable medical device satisfies an implantation criterion, the implantable medical device including: the housing, control electronics encased within the housing, and a lead coupled to the housing; and
disclosing to a user, with the computer system, whether the implantation site for the housing satisfies the implantation criterion;
wherein evaluating, as a function of the at least one image, whether the implantation site satisfies the implantation criterion includes identifying, with the computer system, based on the at least one image, one or more of skull curvature, skull thickness, scalp thickness, locations of one or more vascular structures within the scalp, or locations of one or more nerves within the scalp, and evaluating, with the computer system, whether the implantation site satisfies the implantation criterion based on the one or more of the skull contour, skull thickness, scalp thickness, locations of one or more vascular structures within the scalp, or locations of one or more nerves within the scalp.

21. The method of claim 20, wherein receiving the at least one image comprises receiving an image generated by at least one of X-ray, magnetic resonance imaging, CT-scan, or fluoroscopy.

22. The method of claim 20, further comprising, evaluating, with the computer system, as a function of the at least one image, whether the patient is a candidate for implantation of the implantable medical device deployed in a recess created in the skull.

23. The method of claim 20, further comprising, evaluating, with the computer system, based on the at least one image, whether there are any irregularities in the skull or the scalp of the patient that would impede implantation of the implantable medical device.

24. The method of claim 20, further comprising, selecting, with the computer system, from a plurality of configurations of the implantable medical device, one of the configurations of the implantable medical device as a function of the at least one image.

25. The method of claim 24, wherein the plurality of configurations includes a configuration of at least three modules in a triangular configuration and a configuration of at least two modules in a linear configuration.

26. The method of claim 24, wherein selecting one of the configurations includes selecting the configuration as a function of one or more of skull contour, skull thickness, scalp thickness, locations of one or more vascular structures, or locations of one or more neurological structures indicated by the at least one image.

27. The method of claim 20, wherein the at least one image of the head of the patient includes an image of a scalp of the patient.

28. The method of claim 20, further comprising:
evaluating, with the computer system, skull contour data based on the at least one image of the head;
proposing, with the computer system, as a function of the skull contour data, the implantation site for the housing; and
disclosing, with the computer system, the proposed implantation site to the user.

29. The method of claim 20, further comprising:
receiving, with the computer system, the implantation criterion; and
proposing, with the computer system, at least the implantation site for the housing based on the implantation criterion and the one or more of the skull contour, skull thickness, scalp thickness, locations of one or more vascular structures within the scalp, or locations of one or more nerves within the scalp.

30. The method of claim 29, further comprising:
proposing, with the computer system, a second implantation site for the housing based on the implantation criterion and the one or more of the skull contour, skull thickness, scalp thickness, locations of one or more vascular structures within the scalp, or locations of one or more nerves within the scalp.

31. The method of claim 20, wherein the implantation criterion comprises one or more potential incision locations.

32. The method of claim 20, further comprising receiving, with the computer system, an indication of the implantation site from the user.

33. The method of claim 20, wherein the at least one image of the head of the patient includes a soft-tissue image and a hard-tissue image of the head of the patient.

34. The method of claim 20, wherein evaluating, as a function of the at least one image, whether the implantation site satisfies the implantation criterion includes identifying, based on the at least one image, the skull curvature and evaluating whether the implantation site satisfies the implantation criterion based on the skull curvature.

35. The method of claim 20, wherein evaluating, as a function of the at least one image, whether the implantation site satisfies the implantation criterion includes identifying, based on the at least one image, the skull thickness and evaluating whether the implantation site satisfies the implantation criterion based on the skull thickness.

36. The method of claim 20, wherein evaluating, as a function of the at least one image, whether the implantation site satisfies the implantation criterion includes identifying, based on the at least one image, the scalp thickness and evaluating whether the implantation site satisfies the implantation criterion based on the scalp thickness.

37. The method of claim 20, wherein evaluating, as a function of the at least one image, whether the implantation site satisfies the implantation criterion includes identifying, based on the at least one image, the locations of one or more vascular structures within the scalp and evaluating whether the implantation site satisfies the implantation criterion based on the locations of one or more vascular structures within the scalp.

38. The method of claim 20, wherein evaluating, as a function of the at least one image, whether the implantation site satisfies the implantation criterion includes identifying, based on the at least one image, the locations of one or more nerves within the scalp and evaluating whether the implantation site satisfies the implantation criterion based on the locations of one or more nerves within the scalp.

39. The method of claim 20, further comprising implanting at least the housing of the medical device at the implantation site.

40. The method of claim 39, wherein the implantable medical device includes an implantable neurostimulator.

41. The method of claim 20, further comprising:
generating a model of the skull of the patient as a function of the at least one image of the head of the patient; and
providing the implantable medical device as a function of the model of the skull.

42. The method of claim 41,
wherein generating the model of the skull comprises generating a physical model of the skull, and
wherein providing the implantable medical device comprises adjusting a standard configuration of the implantable medical device to fit the physical model of the skull.

43. The method of claim 41, wherein generating the model of the skull comprises generating, with the computer system, a virtual model of the skull.

44. The method of claim 20, further comprising:
selecting, with the computer system, an incision site for the implantation site as a function of the evaluation of the one or more of skull curvature, skull thickness, scalp thickness, locations of one or more vascular structures within the scalp, or locations of one or more nerves within the scalp; and
indicating, with the computer system, the incision site to the user.

45. The method of claim 20, wherein the implantable medical device includes an implantable neurostimulator.

* * * * *